(12) United States Patent
Kanda

(10) Patent No.: US 11,607,177 B2
(45) Date of Patent: Mar. 21, 2023

(54) ELECTRONIC APPARATUS, CONTROL METHOD, AND PROGRAM

(71) Applicant: KYOCERA Corporation, Kyoto (JP)

(72) Inventor: Toui Kanda, Tokyo (JP)

(73) Assignee: Kyocera Corporation, Kyoto (JP)

( * ) Notice: Subject to any disclaimer, the term of this patent is extended or adjusted under 35 U.S.C. 154(b) by 1001 days.

(21) Appl. No.: 16/335,068

(22) PCT Filed: Sep. 27, 2017

(86) PCT No.: PCT/JP2017/035069
§ 371 (c)(1),
(2) Date: Mar. 20, 2019

(87) PCT Pub. No.: WO2018/062323
PCT Pub. Date: Apr. 5, 2018

(65) Prior Publication Data
US 2019/0274629 A1    Sep. 12, 2019

(30) Foreign Application Priority Data

Sep. 27, 2016 (JP) .............................. JP2016-188621

(51) Int. Cl.
*A61B 5/1455* (2006.01)
*A61B 5/00* (2006.01)
*A61B 5/026* (2006.01)
*G01N 21/47* (2006.01)
*G01N 33/49* (2006.01)
(Continued)

(52) U.S. Cl.
CPC .............. *A61B 5/7221* (2013.01); *A61B 5/00* (2013.01); *A61B 5/02* (2013.01); *A61B 5/0261* (2013.01); *A61B 5/0285* (2013.01); *A61B 5/6814* (2013.01); *A61B 5/6826* (2013.01); *G01N 21/47* (2013.01); *G01N 33/49* (2013.01); *A61B 2562/0233* (2013.01); *G01N 2021/473* (2013.01)

(58) Field of Classification Search
CPC ... A61B 5/7221; A61B 5/7207; A61B 5/0261; A61B 5/02; A61B 5/026; A61B 5/00; A61B 5/7257; A61B 5/6826; A61B 5/6814
See application file for complete search history.

(56) References Cited

U.S. PATENT DOCUMENTS 5,575,285 A * 11/1996 Takanashi .......... A61B 5/14551
600/323
6,173,197 B1 1/2001 Boggett et al.
7,438,688 B2 10/2008 Kobayashi et al.
(Continued)

FOREIGN PATENT DOCUMENTS

CN       101766497 A      7/2010
GB       2351197 A       12/2000
(Continued)

*Primary Examiner* — Chu Chuan Liu
(74) *Attorney, Agent, or Firm* — Volpe Koenig

(57) ABSTRACT

An electronic apparatus includes an output interface and a controller. The output interface is configured to output a signal on the basis of scattered light from a measured part. The controller is configured to calculate a temporal change of a power spectrum on the basis of the signal and detect noise included in the signal on the basis of the temporal change of the power spectrum.

20 Claims, 8 Drawing Sheets

(51) Int. Cl.
    *A61B 5/0285*     (2006.01)
    *A61B 5/02*     (2006.01)

(56) References Cited

U.S. PATENT DOCUMENTS

| | | | |
|---|---|---|---|
| 2002/0183627 A1* | 12/2002 | Nishii | A61B 5/0261 600/485 |
| 2007/0060827 A1 | 3/2007 | Kobayashi et al. | |
| 2013/0096464 A1 | 4/2013 | Tanaka et al. | |

FOREIGN PATENT DOCUMENTS

| | | |
|---|---|---|
| JP | 2007-054471 A | 3/2007 |
| JP | 2013-150772 A | 8/2013 |
| WO | 2011/155048 A1 | 12/2011 |

* cited by examiner

ELECTRONIC APPARATUS, CONTROL METHOD, AND PROGRAM

CROSS REFERENCE TO RELATED APPLICATION

This application claims priority to and the benefit of Japanese Patent Application No. 2016-188621 (filed on Sep. 27, 2016), the entire contents of which are incorporated herein by reference.

TECHNICAL FIELD

The present disclosure relates to an electronic apparatus, a control method, and a program.

BACKGROUND

Apparatuses configured to remove noise from data associated with biological information acquired from a subject (a user) are conventionally known.

SUMMARY

An electronic apparatus according to one embodiment includes an output interface and a controller. The output interface is configured to output a signal on the basis of scattered light from a measured part. The controller is configured to calculate a temporal change of a power spectrum on the basis of the signal and detect noise included in the signal on the basis of the temporal change of the power spectrum.

A control method according to one embodiment includes a step of receiving a signal output on the basis of scattered light from a measured part, a step of calculating a temporal change of a power spectrum on the basis of the signal, and a step of detecting noise included in the signal on the basis of the temporal change of the power spectrum.

A program according to one embodiment causes a computer to execute a step of receiving a signal output on the basis of scattered light from a measured part, a step of calculating a temporal change of a power spectrum on the basis of the signal, and a step of detecting noise included in the signal on the basis of the temporal change of the power spectrum.

DETAILED DESCRIPTION

Hereinafter, an embodiment of the present disclosure will be described in detail with reference to the accompanying drawings.

Figure 1:
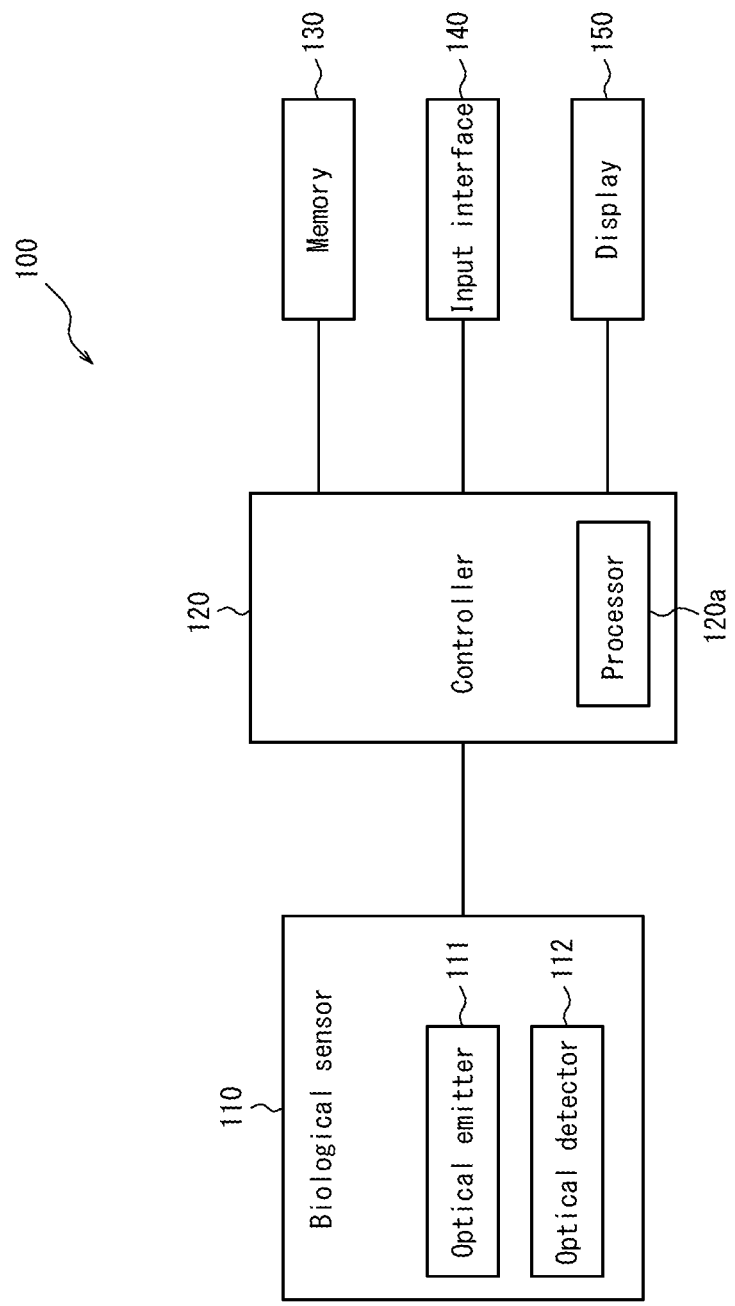
FIG. 1 is a functional block diagram illustrating a schematic configuration of an electronic apparatus according to one embodiment of the present disclosure.

FIG. 1 is a functional block diagram illustrating a schematic configuration of an electronic apparatus 100 according to an embodiment of the present disclosure. The electronic apparatus 100 includes a biological sensor 110, a controller 120, a memory 130, an input interface 140, and a display 150.

The electronic apparatus 100 measures biological information of a subject. The electronic apparatus 100 measures the biological information on the basis of biological information data (hereinafter, also referred to simply as "data") acquired by the biological sensor 110. The electronic apparatus 100 acquires the data in a state in which, for example, the biological sensor 110 is in contact with a measured part such as a finger or a forehead. The biological information measured by the electronic apparatus 100 is information about any living organism that can be measured using data acquired by the biological sensor 110. Although in the present embodiment the biological information is described as information about blood flow amount, the biological information is not limited thereto.

The biological sensor 110 acquires the data. The biological sensor 110 acquires the data in a state, for example, in which it contacts the measured part. The biological sensor 110 may be equipped with an optical emitter 111 and an optical detector 112. The biological sensor 110 irradiates the measured part with measurement light and receives reflected light (scattered light) from an inner tissue of the measured part. The biological sensor 110 transmits a photoelectric conversion signal of the scattered light to the controller 120. The biological sensor 110 functions as an output interface configured to output a signal based on the scattered light.

The optical emitter 111 irradiates the measured part with measurement light on the basis of control performed by the controller 120. The optical emitter 111 irradiates the measured part with measurement light such as laser light at a wavelength that enables the detection of a predetermined blood component. The optical emitter 111 may be configured as, for example, an LD (Laser Diode).

The optical detector 112 receives the scattered light of the measurement light from the measured part. The optical detector 112 may be configured as, for example, a PD (Photo Diode). A photoelectronic conversion signal of the scattered light received by the optical detector 112 is transmitted to the controller 120.

The controller 120 includes at least one processor 120a configured to control and manage the electronic apparatus 100 in its entirety including each functional block thereof. The controller 120 is configured to include at least one processor 120a such as a CPU (Central Processing Unit) which executes a program defining a control procedure to realize the functionality. Such a program is stored in, for example, the memory 130 or an external storage medium coupled to the electronic apparatus 100.

In various embodiments, the at least one processor 120a may be realized as a single integrated circuit (IC), or a plurality of ICs and/or discrete circuits communicably coupled to one another. The at least one processor 120a may be realized according to various known technologies.

In one embodiment, the processor 120a includes one or more circuits or units configured to execute one or more data computing procedures or process by executing instructions stored in an associated memory. In some embodiments, the processor 120a may be configured as firmware (e.g., discrete logic components) configured to execute one or more data computing procedures or process.

In various embodiments, in order to perform the function of the controller 120, the processor 120a may include one or more processors, controllers, microprocessors, microcontrollers, ASICs (application specific integrated circuits), digital signal processors, programmable logic devices, or field programmable gate arrays, any combination thereof, or any combination of configurations thereof. The processor 120a may include any combination of other know devices or any combination of configurations thereof.

The controller 120 measures (calculates) the biological information on the basis of the data acquired from the biological sensor 110. The controller 120 may measure the blood flow amount as the biological information. However, the biological information is not limited to the blood flow amount. The controller 120 detects noise in the data when biological information is measured. The noise detection performed by the controller 120 will be described in detail later.

When the controller 120 detects noise in the data, the controller 120 corrects the data by removing the noise. A correction method for the data performed by the controller 120 will be described in detail later. Because the controller 120 corrects the data by removing the noise, the measurement accuracy of the biological information performed by the electronic apparatus 100 is improved.

The memory 130 may be configured as a semiconductor memory or a magnetic memory. The memory 130 stores various information and/or programs for operating the electronic apparatus 100. The memory 130 may also function as a working memory. The memory 130 may store, for example, the data acquired by the biological sensor 110.

The input interface 140 receives an input operation performed by the subject and is configured, for example, as an operation button (an operation key). When the input interface 140 is configured as a touch panel, the input interface 140 may display an operation button for receiving an input operation performed by the subject on a display device and receive a touch input operation.

The display 150 is a display device configured as, for example, a liquid crystal display, an organic EL (Electro Luminescent) display, or an inorganic EL display. The display 150 displays, for example, a result of the measurement of the biological information performed by the electronic apparatus 100.

Next, a blood flow rate measurement technique using Doppler shift employed by the controller 120 will be described.

In the tissues of the living body, scattered light scattered by moving blood cells undergoes a frequency shift (a Doppler shift) due to a Doppler effect that is proportional to the moving speed of the blood cells in the blood. The controller 120 detects a beat signal generated by light interference between scattered light from static tissues and scattered light from the moving blood cells. The beat signal represents intensity as a function of time. The controller 120 converts the beat signal into a power spectrum which represents power as a function of frequency. In the power spectrum of the beat signal, the Doppler shift frequency is proportional to the moving speed of the blood cells. In the power spectrum of the beat signal, the power corresponds to the amount of blood cells. The controller 120 acquires the blood flow amount by multiplying the power spectrum of the beat signal by the frequency and then integrating the multiplication result.

Figure 2A:
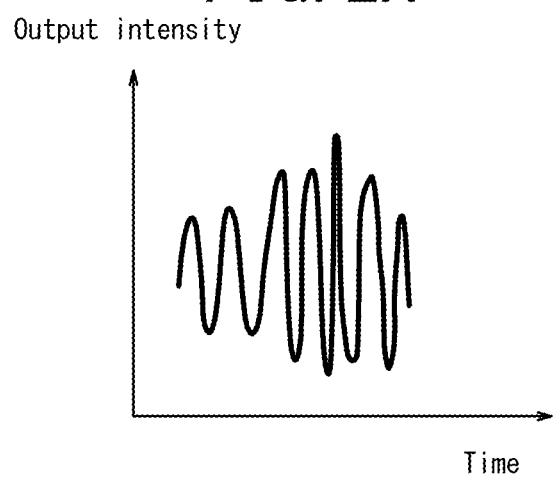
FIG. 2A is a schematic diagram illustrating a blood flow amount measurement process performed by the electronic apparatus of FIG. 1.
Figure 2B:
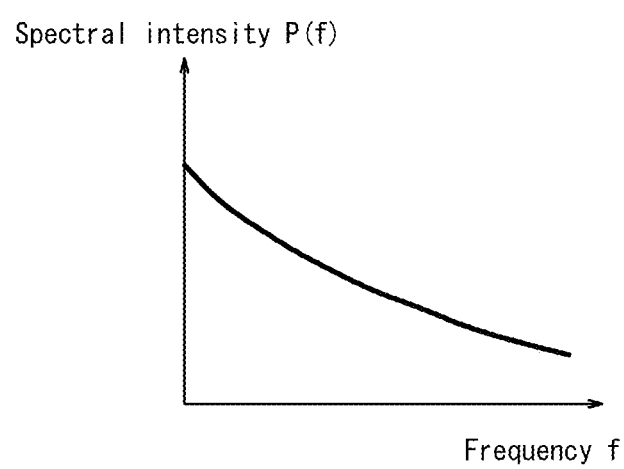
FIG. 2B is a schematic diagram illustrating the blood flow amount measurement process performed by the electronic apparatus of FIG. 1.
Figure 2C:
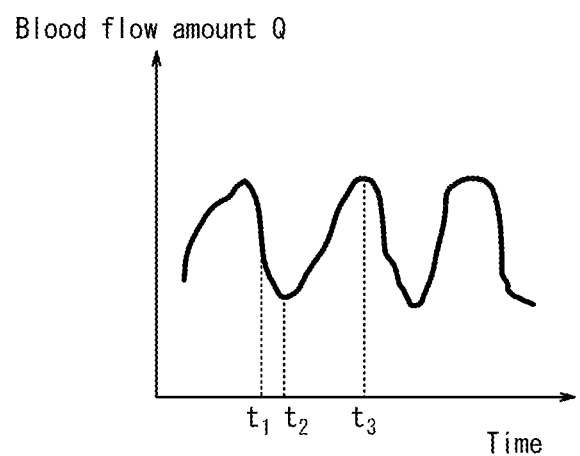
FIG. 2C is a schematic diagram illustrating the blood flow amount measurement process performed by the electronic apparatus of FIG. 1.

FIG. 2A to FIG. 2C are schematic diagrams illustrating the blood flow amount measurement process performed by the electronic apparatus 100. FIG. 2A is a diagram illustrating an example of the photoelectric conversion signal acquired by the controller 120 from the optical detector 112. In FIG. 2A, the vertical axis represents output intensity of the optical detector 112 (i.e., intensity of the scattered light received by the optical detector 112), and the horizontal axis represents time. The controller 120 calculates the power spectrum of the output intensity on the basis of the output of the optical detector 112 as illustrated in FIG. 2A by way of example.

FIG. 2B is a diagram illustrating an example of the power spectrum calculated by the controller 120. The controller 120 calculates the power spectrum as illustrated in FIG. 2B by performing a Fast Fourier Transform on the output intensity. In FIG. 2B, the vertical axis represents spectral intensity P(f), and the horizontal axis represents frequency f. The power spectrum shows, for example, a distribution with a downward descent to the right as illustrated in FIG. 2B. The controller 120 calculates the power spectrum of the output intensity at predetermined intervals (e.g., every 0.1024 seconds, that is, the time to collect 2048 data points by sampling at 20 kHz). The controller 120 calculates the blood flow amount on the basis of the power spectrum as illustrated in FIG. 2B.

FIG. 2C is a diagram illustrating an example of the flood flow amount calculated by the controller 120. In FIG. 2C, the vertical axis represents the blood flow amount Q, and the horizontal axis represents time. The controller 120 calculates the blood flow amount using, for example, the following equation (1).

[Equation 1]

$$Q = \Sigma f \times P(f) \tag{1}$$

During the measurement of the biological information, when the positional relationship between the biological sensor 110 that acquires the data and the measured part (skin) changes, the output intensity received by the optical detector 112 also changes. That is, the optical detector 112 detects the beat signal caused by moving blood cells as referred to in the above description of the blood flow amount measurement technique using the Doppler shift, but may also detect, as the beat signal, the change (a deviation) of the positional relationship between the biological sensor 110 and the measured site. Such a beat signal caused by the deviation of the biological sensor 110 from the measured part is noise that causes a deterioration in the measurement accuracy of the biological information. Hereinafter, such noise is also referred to as a body-movement noise.

Figure 3:
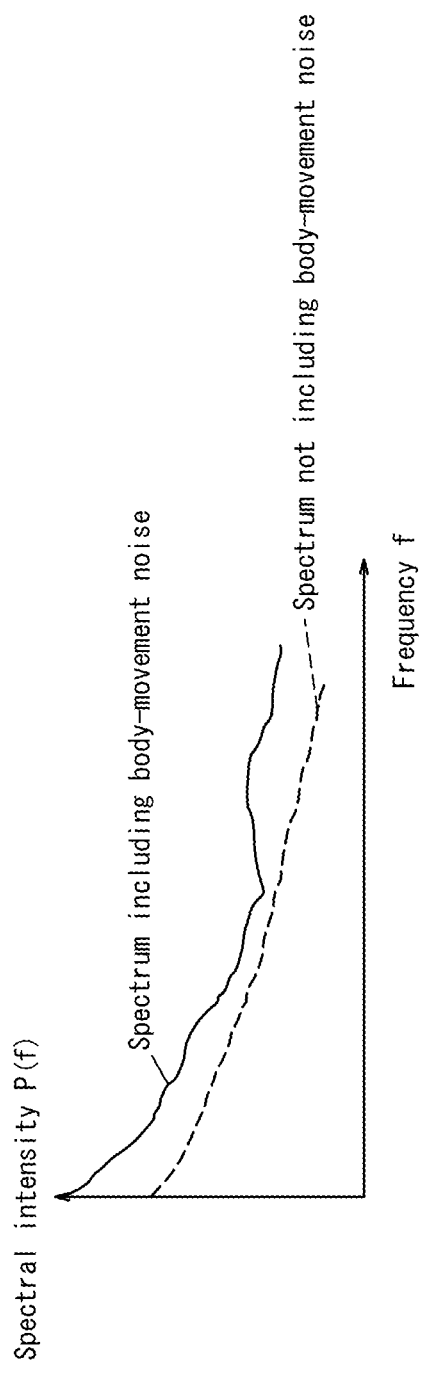
FIG. 3 is a diagram illustrating an example spectrum that includes a body-movement noise.

When body-movement noise is generated, the spectral intensity P(f) increases as illustrated in FIG. 3 by way of example. The body-movement noise affects all frequency bands as illustrated in FIG. 3. That is, the body-movement noise does not affect only a particular frequency band. Accordingly, the use of a frequency band selective filter for processing a particular frequency band such as a band-pass filter cannot adequately remove the body-movement noise.

Next, the noise detection and the correction performed by the controller 120 according to the present embodiment will be described in detail. The controller 120 detects body-movement noise on the basis of a change of the spectrum. When controller 120 detects body-movement noise, the controller 120 corrects the spectrum that includes the body-movement noise as illustrated in FIG. 3 by way of example and generates a spectrum that does not include the body-movement noise.

The controller 120 performs the noise detection and the correction by calculating a temporal change of the power spectrum. The controller 120 may calculate the temporal changes of at least three frequencies of the power spectrum. Here, it is assumed that the controller 120 calculates the temporal changes of at least three frequencies of the power spectrum. The three frequencies for which the controller 120 calculates the temporal change are a low frequency $f_l$, a medium frequency $f_m$, and a high frequency $f_h$, in ascending order of the frequency. The low frequency $f_l$ is, for example, a frequency of several tens of Hz. The medium frequency $f_m$ is, for example, a frequency of 7 kHz to 10 kHz. The high frequency $f_h$ is, for example, a frequency of 18 kHz to 20 kHz. Note that these frequencies are used by way of example only, and the frequencies for which the controller 120 calculates the temporal change may be frequencies in other frequency bands.

Figure 4:
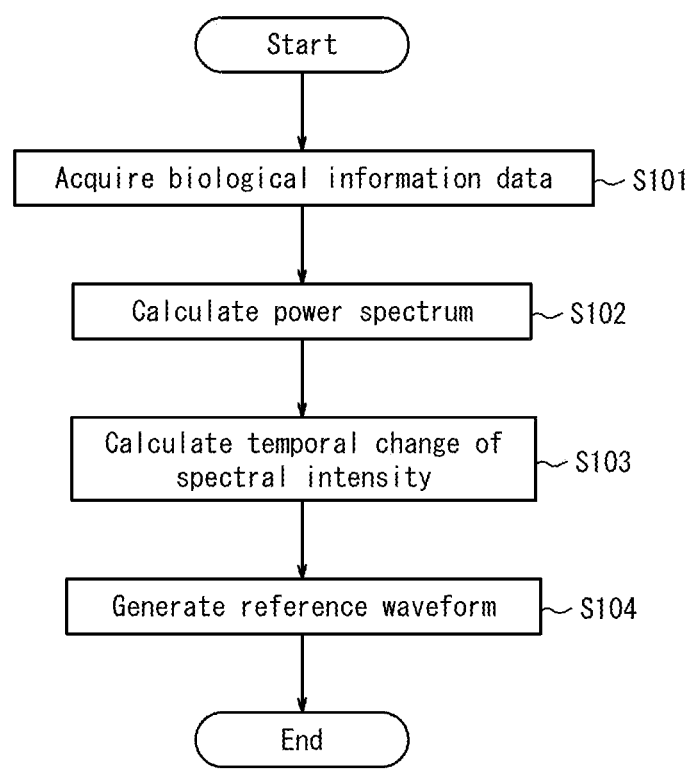
FIG. 4 is a flowchart illustrating an example process for generating a reference waveform of a temporal change of a power spectrum performed by the electronic apparatus of FIG. 1.

In order to perform the noise detection and the correction process, the controller 120 first generates reference waveforms for the temporal changes of the power spectrum to be used as basis for the noise detection. FIG. 4 is a flowchart illustrating an example generation process for the reference waveforms.

The controller 120 acquires the data from the biological sensor 110 (step S101).

The controller 120 calculates the power spectrum on the basis of the data by employing the foregoing method or the like (step S102).

The controller 120 calculates the temporal changes of the spectral intensity P(f) of the low frequency $f_l$, the medium frequency $f_m$, and the high frequency $f_h$, on the basis of the power spectrum (step S103).

Figure 5A:
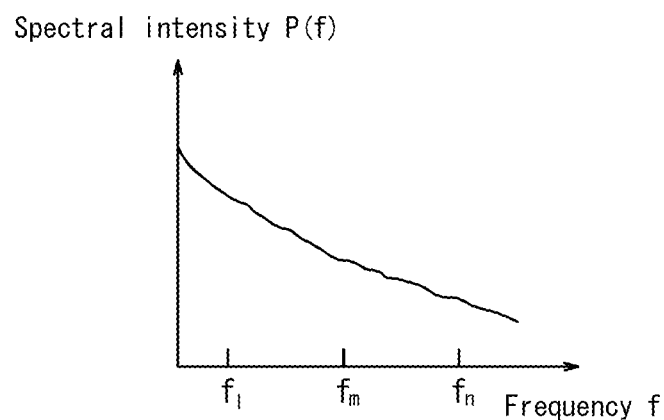
FIG. 5A is a diagram illustrating an example power spectrum.

Here, the temporal change of the power spectrum calculated by the controller 120 will be described with reference to FIG. 5A to FIG. 5C. The waveform of the blood flow amount has a shape that oscillates between peaks and valleys with time, as illustrated in FIG. 2C by way of example. The power spectrum at the midpoint (the center) of the oscillation of the waveform of the power spectrum, e.g., the power spectrum at the time $t_1$ of FIG. 2C, has the shape as illustrated in FIG. 5A.

Figure 5B:
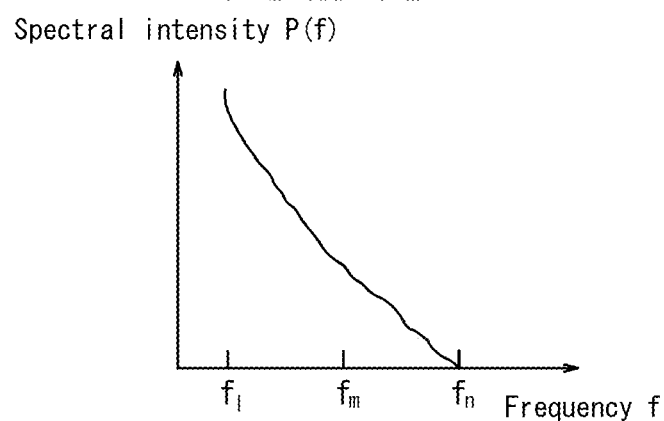
FIG. 5B is a diagram illustrating an example power spectrum.

The power spectrum at the valley of the waveform of the blood flow amount, e.g., the power spectrum at the time $t_2$ of FIG. 2C, has the shape as illustrated in FIG. 5B. As can be understood with reference to FIG. 5A and FIG. 5B, in the power spectrum at the valley the spectral intensity P(f) of the low frequency $f_l$ is higher and the spectral intensity P(f) of the high frequency $f_h$ is lower, as compared to the power spectrum P(f) at the midpoint of the oscillation.

Figure 5C:
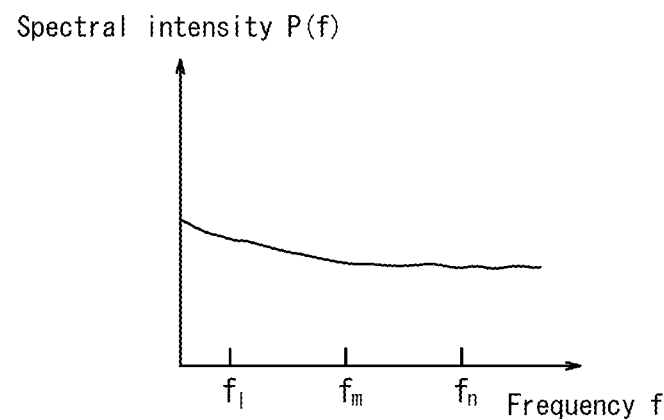
FIG. 5C is a diagram illustrating an example power spectrum.

The power spectrum at the peak of the waveform of the blood flow amount, e.g., the power spectrum at the time of time $t_3$ of FIG. 2C, has the shape as illustrated in FIG. 5C. As can be understood with reference to FIG. 5A to FIG. 5C, in the power spectrum at the peak, the spectral intensity P(f) of the low frequency $f_l$ is lower and the spectral intensity P(f) of the high frequency $f_h$ is higher, as compared to the power spectrum P(f) at the midpoint of the oscillation.

Figure 6A:
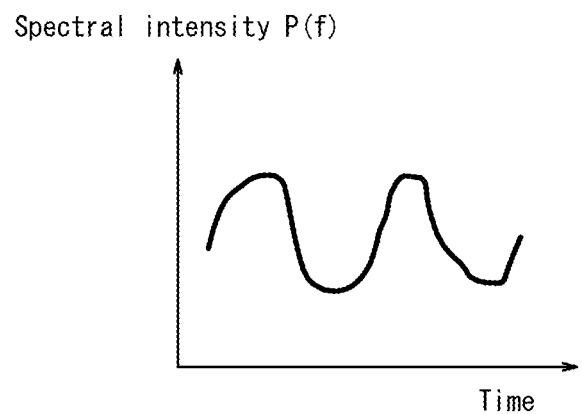
FIG. 6A is a diagram illustrating an example temporal change of spectral intensity.
Figure 6B:
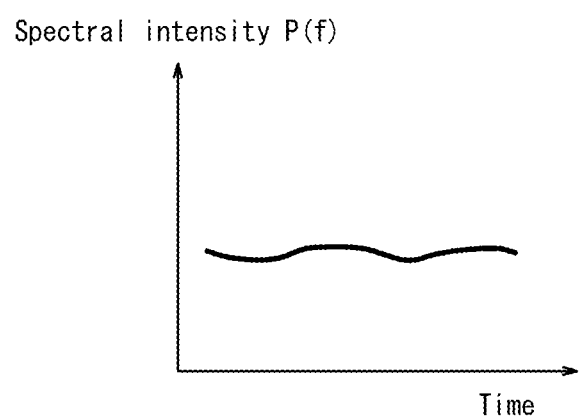
FIG. 6B is a diagram illustrating an example temporal change of the spectral intensity.
Figure 6C:
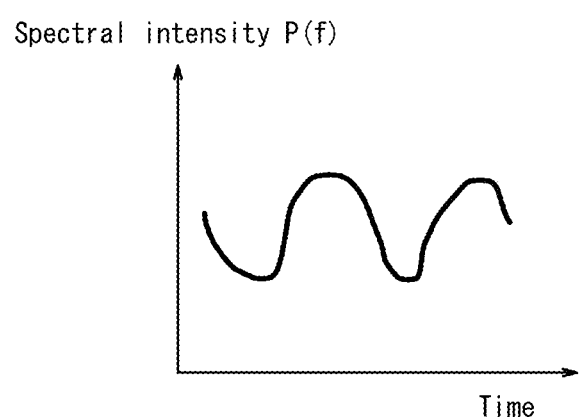
FIG. 6C is a diagram illustrating an example temporal change of the spectral intensity.

FIG. 6A to FIG. 6C are diagrams illustrating examples of the temporal change of the spectral intensity P(f). FIG. 6A, FIG. 6B, and FIG. 6C illustrate the temporal changes of the spectral intensity P(f) of the low frequency $f_l$, the medium frequency $f_m$, and the high frequency $f_h$, respectively. As can be understood with reference to FIG. 6A to FIG. 6C, the spectral intensity P(f) of each of the low frequency $f_l$ and the high frequency $f_h$ has a waveform that oscillates from high to low with time. When the spectral intensity P(f) of the low frequency $f_l$ is at a peak, the spectral intensity P(f) of the high frequency $f_h$ is at a peak. On the other hand, when the spectral intensity P(f) of the low frequency $f_l$ is at a valley, the spectral intensity P(f) of the high frequency fl is at a valley. As can be understood with reference to FIG. 6B, the spectral intensity P(f) of the medium frequency $f_m$ is substantially constant. The medium frequency $f_m$ may be a frequency that has spectral intensity P(f) substantially constant with time.

The controller 120 generates the reference waveforms on the basis of the temporal changes of the spectral intensity P(f) calculated in step S103 (step S104). In particular, the controller 120 generates the reference waveforms by predicting the temporal changes of the spectral intensity P(f) of the low frequency $f_l$, the medium frequency $f_m$, and the high frequency $f_h$, and determining the predicted temporal changes of the spectral intensity P(f) as the reference waveforms. In this manner, the controller 120 generates the reference waveforms on the basis of past data. The reference waveforms may be generated at, for example, predetermined time intervals. The controller 120 can generate the reference waveforms that reflect a trend of the spectral intensity P(f) by generating the reference waveforms at the predetermined time intervals. Note that the trend of the spectral intensity P(f) includes rise and fall of the midpoint of the oscillation, a change of amplitude, a change of a oscillation period, and the like.

Figure 7:
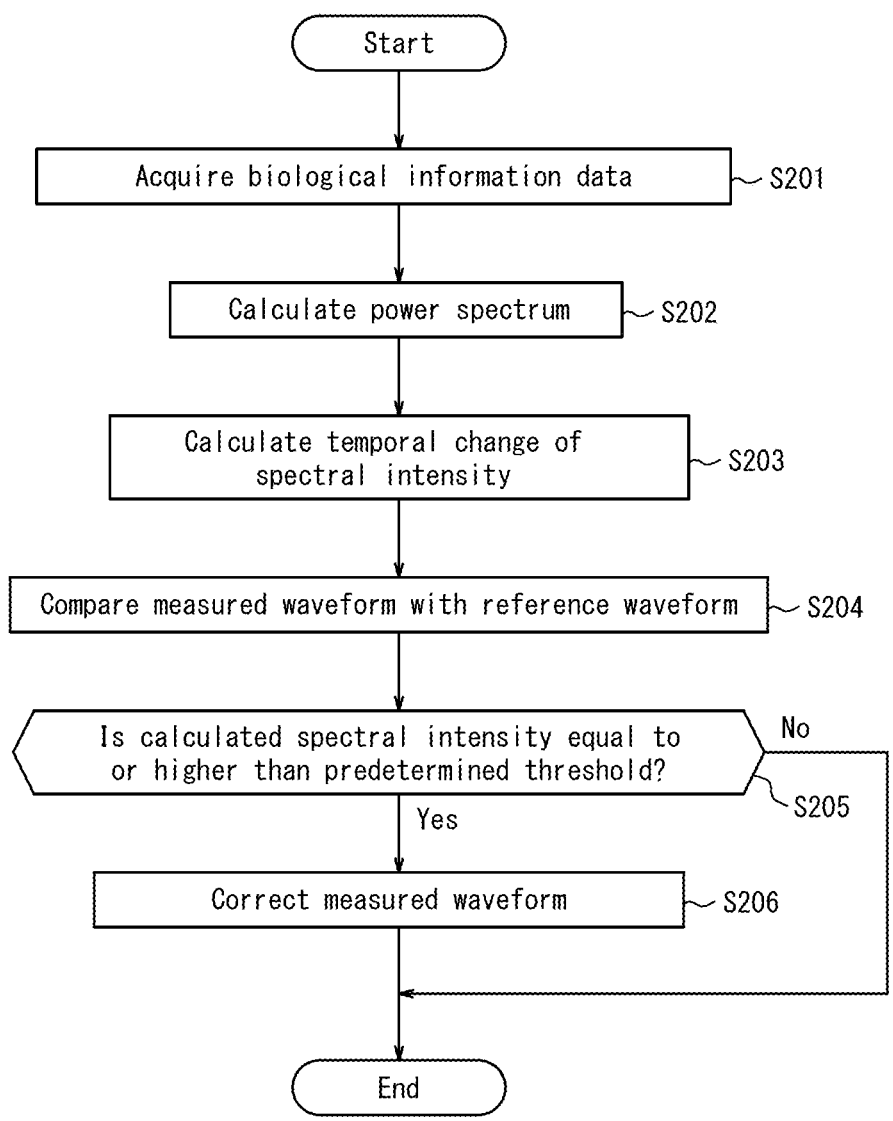
FIG. 7 is a flowchart illustrating noise detection and a correction process by way of example performed by the electronic apparatus of FIG. 1.

After generating the reference waveforms, the controller 120 performs the noise detection and correction using the reference waveforms. FIG. 7 is a flowchart illustrating the noise detection and correction by way of example.

The controller 120 acquires the data from the biological sensor 110 (step S201).

The controller 120 calculates the power spectrum on the basis of the data by employing the foregoing method or the like (step S202).

The controller 120 calculates the temporal changes of the spectrum P(f) at the low frequency $f_l$, the medium frequency $f_m$, and the high frequency $f_h$, on the basis of the power spectrum (step S203). Here, the waveforms of the temporal change of the spectral intensity P(f) calculated in step S203 are referred to as measured waveforms.

The controller 120 detects the body-movement noise on the basis of the measured waveforms calculated in step S203. In particular, the controller 120 detects the body-movement noise on the basis of a comparison between the measured waveforms calculated in step S203 and the reference waveforms generated in step S104 of FIG. 4.

That is, the controller 120 first compares the measured waveforms calculated in step S203 and the reference waveforms generated in step S104 of FIG. 4 (step S204).

The controller 120 determines whether the body-movement noise is being generated, on the basis of the comparison. For example, the controller 120 provides a threshold associated with the reference waveforms and determines whether the spectral intensity P(f) at a predetermined time calculated in step S203 is equal to or higher than the threshold (step S205). The controller 120 may determine that the body-movement noise is being generated at a time at which the spectral intensity P(f) is equal to or higher than the threshold. That is, the controller 120 determines that a time slot in which the spectral intensity P(f) of the measured waveform is higher than the reference waveform by the threshold or more is a time slot in which the body-movement noise is generated.

Figure 8A:
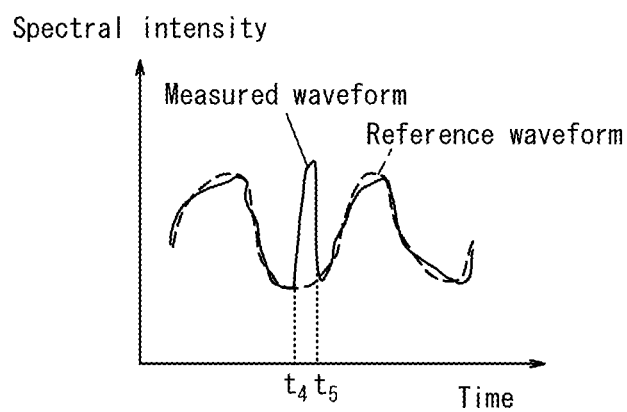
FIG. 8A is a diagram schematically illustrating the noise detection performed by the electronic apparatus of FIG. 1.
Figure 8B:
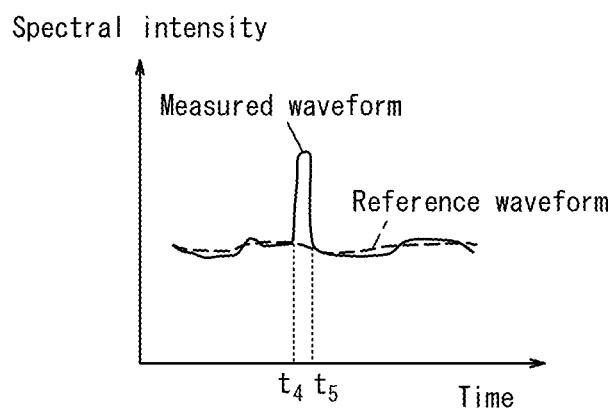
FIG. 8B is a diagram schematically illustrating the noise detection performed by the electronic apparatus of FIG. 1.
Figure 8C:
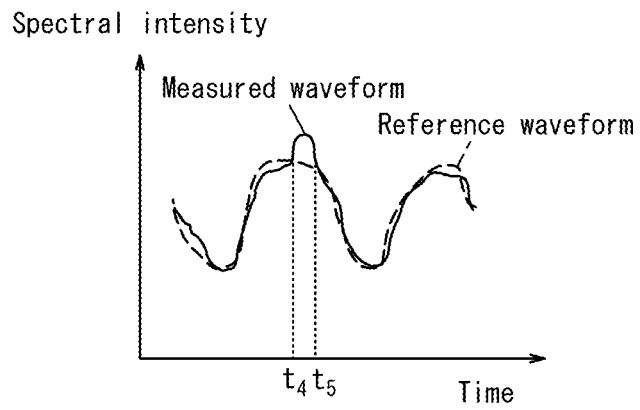
FIG. 8C is a diagram schematically illustrating the noise detection performed by the electronic apparatus of FIG. 1.

FIG. 8A to FIG. 8C are schematic diagrams illustrating the noise detection performed by the electronic apparatus 100. FIG. 8A, FIG. 8B, and FIG. 8C illustrate the temporal changes of the spectral intensity P(f) of the low frequency $f_l$, the medium frequency $f_m$, and the high frequency $f_h$. Each of FIG. 8A to FIG. 8C illustrates the reference waveform and the measured waveform. When the spectral intensity of the measured waveform is higher than the spectral intensity P(f) of the reference waveform by the threshold or more in a time zone between $t_4$ and $t_5$ as illustrated in FIG. 8A to FIG. 8C, the controller 120 determines that body-movement noise is being generated in the time slot between time t4 and time t5.

When the controller 120 determines that the spectral intensity P(f) calculated in step S203 is higher by the above threshold or more (a Yes determination in step S205), the controller 120 may determine that the noise is generated in the time slot in which the spectral intensity P(f) is higher by the above threshold or more. In this case, the controller 120 corrects the measured waveform (step S206). The controller 120 may correct the measured waveform in the time slot in which it is determined that the body-movement noise is being generated, by, for example, replacing the measured waveforms with the reference waveforms. The controller 120 may otherwise correct the measured waveform.

When the controller 120 determines that there is no time slot in which the spectral intensity P(f) calculated in step S203 is equal to or higher than the above threshold (a No determination in step S205), the controller 120 determines that body-movement noise is not being generated and ends the flow.

The controller 120 may reproduce the power spectrum as illustrated in FIG. 2B by way of example on the basis of the temporal changes of the spectral intensity P(f) of the low frequency $F_l$, the medium frequency $f_m$, and the high frequency $f_h$ after performing the noise detection and the correction process illustrated in FIG. 7. In particular, the controller 120 reproduces the shape of the power spectrum on the basis of three points of the spectral intensity P(f) for the high frequency $f_l$, the medium frequency $f_m$, and the high frequency $f_h$. The shape of the power spectrum between the three points may be reproduced by, for example, linear approximation.

The controller 120 may further generate the waveform of the blood flow amount as illustrated in FIG. 2C on the basis of the reproduced power spectrum. Thus, the controller 120 may measure the blood flow amount as the biological information.

The electronic apparatus 100 according to the above embodiment calculates the temporal change of the power spectrum on the basis of the data acquired from the biological sensor 110 and detects noise included in the data on the basis of the power spectrum. Thus, the electronic apparatus 100 can detect the time slot in which noise is generated. The electronic apparatus 100 generates the reference waveforms for the temporal changes of the power spectrum and detects noise on the basis of a comparison with the reference waveforms. The reference waveforms reflect the trend in the spectrum of the blood flow amount of the subject. Thus, the electronic apparatus 100 can perform noise detection that reflects the trend in the change of the spectrum of the blood flow amount of the subject. In this way, the electronic apparatus 100 can improve the accuracy of the noise detection. Accordingly, the usability of the electronic apparatus 100 can be improved in comparison to conventional apparatuses.

When the electronic apparatus 100 detects noise, the electronic apparatus 100 can correct the temporal change of the power spectrum in the time slot in which the noise is detected. The correction may be performed by replacing the measured waveform for the time slot in which the noise is detected with the reference waveform. Thus, the electronic apparatus 100 can correct (remove) the noise without using a frequency band selective filter.

One embodiment has been described in order to provide a complete and clear disclosure. However, the appended claims should not be construed as limited to the above embodiment and are configured to realize every possible variations and alternatives that can be conceived by those who are skilled in the art within the scope of the fundamentals shown herein. Each of the requirements shown in some embodiments can be freely combined.

For example, in the above embodiment the controller 120 detects noise using the temporal changes of three frequencies of the power spectrum. However, the controller 120 may detect noise using, for example, temporal changes of four or more frequencies. This improves the reproducibility of the power spectrum when the power spectrum is reproduced by correcting the noise. The controller 120 may detect a noise on the basis of the temporal change(s) of one or two frequencies. This enables the controller 120 to detect noise with a less processing load.

The invention claimed is:

1. An electronic apparatus comprising:
   a sensor including:
      an optical emitter that emits measurement light to irradiate a measured part;
      a detector that receives scattered light from the measured part; and
      an output interface configured to output a signal on the basis of the received scattered light from the measured part; and
   a controller configured to calculate temporal changes of a low frequency that is less than 100 Hz, medium frequency of 7 kHz to 10 kHz and high frequency of 18 kHz to 20 kHz, of a power spectrum on the basis of the signal and detect noise included in the signal on the basis of the temporal changes of the low frequency, medium frequency and high frequency of the power spectrum.

2. The electronic apparatus according to claim 1,
wherein the controller generates a reference for the temporal changes of the power spectrum and detects the noise on the basis of a comparison between the temporal change of the power spectrum and the reference.

3. The electronic apparatus according to claim 2,
wherein the controller generates the reference on the basis of a signal output in the past.

4. The electronic apparatus according to claim 2,
wherein the controller detects the noise when the power spectrum at a predetermined time is higher than the reference by a predetermined threshold or more.

5. The electronic apparatus according to claim 1,
wherein the controller corrects the temporal changes of the power spectrum on the basis of the noise.

6. The electronic apparatus according to claim 1,
wherein the controller calculates temporal changes for at least three frequencies of the power spectrum.

7. The electronic apparatus according to claim 1,
wherein the controller calculates biological information that is a blood flow amount.

8. The electronic apparatus according to claim 1,
wherein the measured part is a finger or a forehead.

9. A control method comprising:
emitting, by an optical emitter, measurement light to irradiate a measured part;
detecting, by a detector scattered light from the measured part;
receiving, by a controller, a signal output on the basis of scattered light from a measured part;
calculating, by the controller, temporal changes of a low frequency that is less than 100 Hz, medium frequency of 7 kHz to 10 kHz and high frequency of 18 kHz to 20 kHz, of a power spectrum on the basis of the signal; and
detecting, by the controller, noise included in the signal on the basis of the temporal changes of the low frequency, medium frequency and high frequency of the power spectrum.

10. The control method according to claim 9,
further comprising generating, by the controller, a reference for each of the temporal changes of the temporal changes of the power spectrum, and
wherein detecting the noise detects the noise on the basis of a comparison between the temporal changes of the power spectrum and the reference.

11. The control method according to claim 10,
wherein generating the reference generates the reference on the basis of a signal output in the past.

12. The control method according to claim 10,
wherein detecting the noise detects the noise when the power spectrum at a predetermined time is higher than the reference by a predetermined threshold or more.

13. The control method according to claim 9,
further comprising correcting, by the controller, the temporal change of the power spectrum on the basis of the noise.

14. The control method according to claim 9,
wherein calculating the temporal changes calculates temporal changes for at least three frequencies of the power spectrum.

15. A non-transitory computer readable storage medium storing a program configured to cause a computer to execute operations comprising:
emitting, by an optical emitter, measurement light to irradiate a measured part;
detecting, by a detector scattered light from the measured part;
receiving, by a controller, a signal output on the basis of scattered light from a measured part;
calculating, by the controller, temporal changes of a low frequency that is less than 100 Hz, medium frequency of 7 kHz to 10 kHz and high frequency of 18 kHz to 20 kHz, of a power spectrum on the basis of the signal; and
detecting, by the controller, noise included in the signal on the basis of the temporal change of the power spectrum.

16. The non-transitory computer readable storage medium according to claim 15,
further causing the computer to perform generating a reference for the temporal change of the power spectrum,
wherein detecting the noise detects the noise on the basis of a comparison between the temporal change of the power spectrum and the reference.

17. The non-transitory computer readable storage medium according to claim 16,
wherein generating the reference generates the reference on the basis of a signal output in the past.

18. The non-transitory computer readable storage medium according to claim 16,
wherein detecting the noise detects the noise when the power spectrum at a predetermined time is higher than the reference by a predetermined threshold or more.

19. The non-transitory computer readable storage medium according to claim 15,
further causing the computer to perform correcting the temporal changes of the power spectrum on the basis of the noise.

20. The non-transitory computer readable storage medium according to claim 15,
wherein calculating the temporal changes calculates temporal changes for at least three frequencies of the power spectrum.

* * * * *